United States Patent
Sakya

(10) Patent No.: US 6,538,009 B2
(45) Date of Patent: Mar. 25, 2003

(54) PYRAZOLE DERIVATIVES AS ANTI-INFLAMMATORY/ANALGESIC AGENTS

(75) Inventor: Subas Man Sakya, East Lyme, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/824,550

(22) Filed: Apr. 2, 2001

(65) Prior Publication Data
US 2002/0115856 A1 Aug. 22, 2002

Related U.S. Application Data
(60) Provisional application No. 60/194,303, filed on Apr. 3, 2000.

(51) Int. Cl.⁷ .................. C07D 401/04; A61K 31/4439
(52) U.S. Cl. ..................................... 514/338; 546/275.7
(58) Field of Search .................. 546/275.7; 514/338

(56) References Cited
U.S. PATENT DOCUMENTS 5,696,143 A * 12/1997 Talley et al. ................ 514/403

* cited by examiner

*Primary Examiner*—Jane Fan
(74) *Attorney, Agent, or Firm*—Peter C. Richardson; Gregg C. Benson; B. Timothy Creagan

(57) ABSTRACT

The present invention relates to compounds of the formula

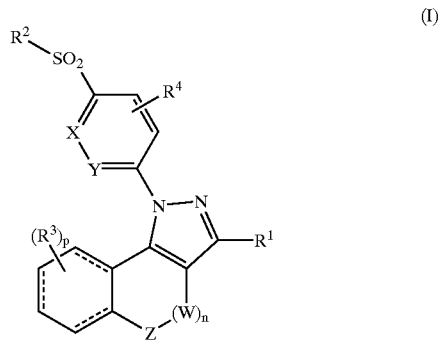

(I)

wherein $R^1$, $R^2$, $R^3$, $R^4$, $R^5$, $R^6$, $R^7$, $R^8$, $R^9$, $R^{10}$, n, p, W, X, Y and Z are defined as in the specification, to pharmaceutical compositions containing them and to their medicinal use. The compounds of the invention are useful in the treatment or alleviation of inflammation and other inflammation associated disorders, such as arthritis, colon cancer, and Alzheimer's disease in mammals, preferably humans, dogs, cats, horses and livestock.

9 Claims, No Drawings

PYRAZOLE DERIVATIVES AS ANTI-INFLAMMATORY/ANALGESIC AGENTS

This application claims priority under 35 U.S.C. §119(e) of U.S. application serial no. 60/194,303, filed Apr. 3, 2000.

BACKGROUND OF THE INVENTION

This invention relates to tricyclic pyrazole derivatives, methods of treatment and pharmaceutical compositions for the treatment of cyclooxygenase mediated diseases. The compounds of this invention inhibit the biosynthesis of prostaglandins by intervention of the action of the enzyme cyclooxygenase on arachidonic acid, and are therefore useful in the treatment or alleviation of inflammation, other inflammation associated disorders, such as arthritis, neurodegeneration and colon cancer, in mammals, preferably humans, dogs, cats, horses or livestock.

Nonsteroidal anti-inflammatory drugs (NSAID's) are widely used in treating pain and the signs and symptoms of arthritis because of their analgesic and anti-inflammatory activity. It is accepted that common NSAID's work by blocking the activity of cyclooxygenase (COX), also known as prostaglandin G/H synthase (PGHS), the enzyme that converts arachidonic acid into prostanoids. Prostaglandins, especially prostaglandin $E_2$ ($PGE_2$), which is the predominant eicosanoid detected in inflammation conditions, are mediators of pain, fever and other symptoms associated with inflammation. Inhibition of the biosynthesis of prostaglandins has been a therapeutic target of anti-inflammatory drug discovery. The therapeutic use of conventional NSAID's is, however, limited due to drug associated side effects, including life threatening ulceration and renal toxicity. An alternative to NSAID's is the use of corticosteroids; however, long term therapy can also result in severe side effects.

The use of NSAID's in dogs and cats has been more limited than that in humans, e.g., only three such NSAID's have been approved by the Food and Drug Administration, Committee on Veterinary Medicine (FDA/CVM), for use in dogs in the United States, i.e., ETOGESIC® (etodolac), ARQUEL® (meclofenamic acid) and RIMADYL® (carprofen). Consequently, there is less experience and knowledge in veterinary medicine about safety and efficacy issues surrounding the use of NSAID's in dogs. In veterinary medicine, for example, the most common indication for NSAID's is the treatment of degenerative joint disease (DJD), which in dogs often results from a variety of developmental diseases, e.g., hip dysplasia and osteochondrosis, as well as from traumatic injuries to joints. In addition to the treatment of chronic pain and inflammation, NSAID's are also useful in dogs for treating post-surgical acute pain, as well as for treating clinical signs associated with osteoarthritis.

Two forms of COX are now known, a constitutive isoform (COX-1) and an inducible isoform (COX-2) of which expression is upregulated at sites of inflammation (Vane, J. R.; Mitchell, J. A.; Appleton, I.; Tomlinson, A.; Bishop-Bailey, D.; Croxtoll, J.; Willoughby, D. A. *Proc. Nat. Acad. Sci. USA*, 1994, 91, 2046). COX-1 is thought to play a physiological role and to be responsible for gastrointestinal and renal protection. On the other hand, COX-2 appears to play a pathological role and is believed to be the predominant isoform present in inflammation conditions. A pathological role for prostaglandins has been implicated in a number of human disease states including rheumatoid arthritis and osteoarthritis, pyrexia, asthma, bone resorption, cardiovascular diseases, dysmenorrhea, premature labor, nephritis, nephrosis, atherosclerosis, hypotension, shock, pain, cancer, and Alzheimer disease. It is believed that compounds that selectively inhibit the biosynthesis of prostaglandins by intervention of the induction phase of the inducible enzyme COX-2 and/or by intervention of the activity of the enzyme COX-2 on arachidonic acid would provide alternate therapy to the use of NSAID's or corticosteroids in that such compounds would exert anti-inflammatory effects without the adverse side effects associated with COX-1 inhibition.

A variety of sulfonylbenzene compounds which inhibit COX are referred to in patent publications (U.S. Pat. Nos. 5,466,823, 5,565,482, 5,670,532 and 5,886,016; PCT publications WO 97/16435, WO 97/14691, WO 96/19469, WO 96/36623, WO 96/03392, WO 96/03387, WO 97/727181, WO 96/936617, WO 96/19469, WO 96/08482, WO 95/00501, WO 95/15315, WO 95/15316, WO 95/15317, WO 95/15318, WO 97/13755, WO 97/11704, and WO 96/09293 and European Patent publication EP 0799523, EP 418845 and EP 554829). Each of the foregoing applications is incorporated herein by reference in its entirety.

SUMMARY OF THE INVENTION

The present invention relates to compounds of the formula

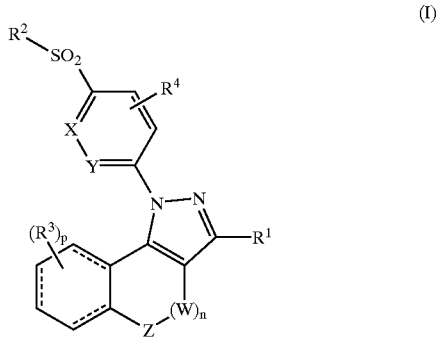

wherein the dashed line represents optional double bonds (which can be between any of the carbon atoms of the ring except that such bonds cannot be cumulative);

n is an integer from zero to four;

p is an integer from one to two;

X is >$CR^7$ or —N—;

Y is >$CR^8$ or —N—;

Z is >$CHR^9$, —O—, —S—, >SO, >$SO_2$, and >$NR^{10}$;

W is >$CR^5R^6$;

$R^1$ is —$CF_3$ or —$CHF_2$;

$R^2$ is ($C_1$–$C_6$)alkyl;

$R^3$ is hydrogen, halo, ($C_1$–$C_6$)alkyl, ($C_2$–$C_6$)alkenyl, ($C_2$–$C_6$)alkynyl, ($C_1$–$C_6$)alkoxy, —$OCF_3$, ($C_1$–$C_6$) alkylcarbonyl, formyl, formamidyl, cyano, ($C_1$–$C_6$) alkoxycarbonyl, aminocarbonyl, N-($C_1$–$C_6$) alkylaminocarbonyl or N,N-[($C_1$–$C_6$) alkyl]$_2$aminocarbonyl;

wherein said $R^3$ ($C_1$–$C_6$)alkyl may optionally be substituted with one to three substituents independently selected from halo, ($C_1$–$C_6$)alkoxy, cyano, ($C_1$–$C_6$) alkoxycarbonyl, aminocarbonyl, N-($C_1$–$C_6$) alkylaminocarbonyl and N,N-[($C_1$–$C_6$) alkyl]$_2$aminocarbonyl;

$R^4$ is hydrogen; halo; hydroxy; ($C_1$–$C_6$)alkyl or ($C_1$–$C_6$) alkoxy optionally substituted with one to three halogen atoms;

wherein said $R^4$ ($C_1$–$C_6$)alkyl group may optionally be substituted with one to three substituents independently selected from halo, hydroxy, ($C_1$–$C_6$)alkoxy and cyano;

$R^5$ is hydrogen, halo, ($C_1$–$C_6$)alkyl, ($C_1$–$C_6$)alkoxy, ($C_1$–$C_6$)alkylcarbonyl, ($C_1$–$C_6$)alkoxycarbonyl or aminocarbonyl;

wherein said $R^5$ ($C_1$–$C_6$)alkyl group may optionally be substituted with one to three substituents independently selected from halo, hydroxy, ($C_1$–$C_6$)alkoxy and cyano;

$R^6$ is hydrogen, halo, ($C_1$–$C_6$)alkyl, ($C_1$–$C_6$)alkoxy, ($C_1$–$C_6$)alkylcarbonyl, ($C_1$–$C_6$)alkoxycarbonyl or aminocarbonyl;

$R^7$ is hydrogen, halo, hydroxy, ($C_1$–$C_6$)alkyl or ($C_1$–$C_6$) alkoxy optionally substituted with one to three halogen atoms;

wherein said $R^7$ ($C_1$–$C_6$)alkyl group may optionally be substituted with one to three substituents independently selected from halo, hydroxy, ($C_1$–$C_6$)alkoxy and cyano;

$R^8$ is hydrogen, halo, hydroxy, ($C_1$–$C_6$)alkyl or ($C_1$–$C_6$) alkoxy optionally substituted with one to three halogen atoms;

wherein said $R^8$ ($C_1$–$C_6$)alkyl group may optionally be substituted with one to three substituents independently selected from halo, hydroxy, ($C_1$–$C_6$)alkoxy and cyano;

$R^9$ is hydrogen, halo, hydroxy, ($C_1$–$C_6$)alkyl or ($C_1$–$C_6$) alkoxy optionally substituted with one to three halogen atoms;

wherein said $R^9$ ($C_1$–$C_6$)alkyl group may optionally be substituted with one to three substituents independently selected from halo, hydroxy, ($C_1$–$C_6$)alkoxy and cyano;

$R^{10}$ is hydrogen, ($C_1$–$C_6$)alkyl, ($C_1$–$C_6$)alkylcarbonyl or aminocarbonyl;

wherein said $R^{10}$ ($C_1$–$C_6$)alkyl group may optionally be substituted with one to three substituents independently selected from halo, hydroxy, ($C_1$–$C_6$)alkoxy and cyano;

with the proviso that at least one of X or Y is —N—;

and the pharmaceutically acceptable salts of such compounds.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds of the invention also exist in different tautomeric forms. This invention relates to all tautomers of formula I.

The compounds of this invention may contain olefin-like double bonds. When such bonds are present, the compounds of the invention exist as cis and trans configurations and as mixtures thereof.

Unless otherwise indicated, the alkyl, referred to herein, as well as the alkyl moieties of other groups referred to herein (e g, alkoxy), may be linear or branched (such as methyl, ethyl, n-propyl, isopropyl, n-butyl, iso-butyl, secondary-butyl, tertiary-butyl), and they may also be cyclic (e.g., cyclopropyl, or cyclobutyl); optionally substituted by 1 to 3 suitable substituents as defined below such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl. The phrase "each of said alkyl" as used herein refers to any of the preceding alkyl moieties within a group such alkoxy, alkenyl or alkylamino. Preferred alkyls include ($C_1$–$C_4$)alkyl, most preferably methyl.

Unless otherwise indicated, halogen includes fluoro, chloro, bromo or iodo, or fluoride, chloride, bromide or iodide.

As used herein, the term "halo-substituted alkyl" refers to an alkyl radical as described above substituted with one or more halogens included, but not limited to, chloromethyl, dichloromethyl, fluoromethyl, difluoromethyl, trifluoromethyl, 2,2,2-trichloroethyl, and the like; optionally substituted by 1 to 3 suitable substituents as defined below such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined below such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl.

As used herein, the term "alkynyl" is used herein to mean straight or branched hydrocarbon chain radicals having one triple bond including, but not limited to, ethynyl, propynyl, butynyl, and the like; optionally substituted by 1 to 3 suitable substituents as defined below such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl.

As used herein, the term "carbonyl" (as used in phrases such as alkylcarbonyl or alkoxycarbonyl) refers to the joinder of the >C=O moiety to a second moiety such as an alkyl or amino group (i.e. an amido group). Alkoxycarbonylamino refers to an alkyl carbamate group. The carbonyl group is also equivalently defined herein as (C=O). Alkylcarbonylamino refers to groups such as acetamide.

As used herein, the term "aryl" means aromatic radicals such as phenyl, naphthyl, tetrahydronaphthyl, indanyl and the like; optionally substituted by 1 to 3 suitable substituents as defined below such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), tetrazole, quinolyl, isoquinolyl, benzothienyl, benzofuryl, indolyl, and the like; optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Particularly preferred heteroaryl groups include pyridyl, thienyl, furyl, thiazolyl and pyrazolyl (these heteroaryls are most preferred of the $R^4$ heteroaryls).

"A suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, $—CO_2H$ groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, an arylsulfonyl groups and the like.

An embodiment (i.e. the tricyclic embodiments)) of the present invention includes compounds of formula I, referred to as the 1,4-Dihydro-indeno[1,2-c]pyrazole Group of compounds, wherein Z is $CHR^9$ and n is zero. Another embodiment of the present invention includes compounds of formula I, referred to as the 4,5-Dihydro-1H-benzo[g]indazole Group of compounds, wherein Z is $CHR^9$ and n is one. Another embodiment of the present invention includes compounds of formula I, referred to as the 1,4,5,6-Tetrahydro-1,2-diaza-benzo[e]azulene Group of compounds, wherein Z is $CHR^9$ and n is two. Another embodiment of the present invention includes compounds of formula I, referred to as the 3H-8-Oxa-2,3-diaza-cyclopenta[a]indene Group of compounds, wherein Z is O and n is zero. Another embodiment of the present invention includes compounds of formula I, referred to as the 1,4-Dihydro-5-oxa-1,2-diaza-cyclopenta[a]naphthalene Group of compounds, wherein Z is O and n is one. Another embodiment of the present invention includes compounds of formula I, referred to as the 1H-Benzo[4,5]thieno[3,2-c]pyrazole Group of compounds, wherein Z is S, and n is zero. Another embodiment of the present invention includes compounds of formula I, referred to as the 1,4-Dihydro-5-thia-1,2-diaza-cyclopenta[a]naphthalene Group of compounds, wherein Z is S, and n is one. Another embodiment of the present invention includes compounds of formula I, referred to as the 1H-Benzo[4,5]thieno[3,2-c]pyrazole 4-oxide Group of compounds, wherein Z is SO, and n is zero. Another embodiment of the present invention includes compounds of formula I, referred to as the 1,4-Dihydro-5-thia-1,2-diaza-cyclopenta[a]naphthalene 5-oxide Group of compounds, wherein Z is SO, and n is one. Another embodiment of the present invention includes compounds of formula I, referred to as the 1H-Benzo[4,5]thieno[3,2-c]pyrazole 4,4-dioxide Group of compounds, wherein Z is $SO_2$, and n is zero. Another embodiment of the present invention includes compounds of formula I, referred to as the 1,4-Dihydro-5-thia-1,2-diaza-cyclopenta[a]naphthalene 5,5-dioxide Group of compounds, wherein Z is $SO_2$, and n is one. Another embodiment of the present invention includes compounds of formula I, referred to as the 1,4-Dihydro-pyrazolo[4,3-b]indole Group of compounds, wherein Z is $>NR^{10}$, and n is zero. Another embodiment of the present invention includes compounds of formula I, referred to as the 4,5-Dihydro-1H-pyrazolo[4,3-c]quinoline Group of compounds, wherein Z is $>NR^{10}$, and n is one.

An embodiment of the present invention includes compounds of formula I, referred to as the Arylsulfonyl Group of compounds, wherein X and Y are both carbon. Another embodiment of the present invention includes compounds of formula I, referred to as the Pyridin-2-yl-sulfonyl Group of compounds, wherein X is nitrogen and Y is carbon. Another embodiment of the present invention includes compounds of formula I, referred to as the Pyridin-3-yl-sulfonyl Group of compounds, wherein Y is nitrogen and X is carbon. Another embodiment of the present invention includes compounds of formula I, referred to as the Pyridazin-2-yl-sulfonyl Group of compounds, wherein X and Y are both nitrogen.

Subgeneric embodiments of the present invention of the Arylsulfonyl Group of compounds are expressly contemplated by the present invention. Such subgeneric embodiments within the Arylsulfonyl Group of compounds include the Arylsulfonyl Group in combination with each of the Tricyclic groups (i.e. 1,4-Dihydro-indeno[1,2-c]pyrazole-Arylsulfonyl Group, 4,5-Dihydro-1H-benzo[g]indazole-Arylsulfonyl Group, 1,4,5,6-Tetrahydro-1,2-diaza-benzo[e]azulene-Arylsulfonyl Group, 3H-8-Oxa-2,3-diaza-cyclopenta[a]indene-Arylsulfonyl Group, 1,4-Dihydro-5-oxa-1,2-diaza-cyclopenta[a]naphthalene-Arylsulfonyl Group, 1H-Benzo[4,5]thieno[3,2-c]pyrazole-Arylsulfonyl Group, 1,4-Dihydro-5-thia-1,2-diaza-cyclopenta[a]naphthalene-Arylsulfonyl Group, 1H-Benzo[4,5]thieno[3,2-c]pyrazole 4-oxide-Arylsulfonyl Group, 1,4-Dihydro-5-thia-1,2-diaza-cyclopenta[a]naphthalene 5-oxide-Arylsulfonyl Group, 1H-Benzo[4,5]thieno[3,2-c]pyrazole 4,4-dioxide-Arylsulfonyl Group, 1,4-Dihydro-5-thia-1,2-diaza-cyclopenta[a]naphthalene 5,5-dioxide-Arylsulfonyl Group, 1,4-Dihydro-pyrazolo[4,3-b]indole-Arylsulfonyl Group and 4,5-Dihydro-1H-pyrazolo[4,3-c]quinoline-Arylsulfonyl Group).

Subgeneric embodiments of the present invention of the Pyridin-2-yl-sulfonyl Group of compounds are expressly contemplated by the present invention. Such subgeneric embodiments within the Pyridin-2-yl-sulfonyl Group of compounds include the Pyridin-2-yl-sulfonyl Group in combination with each of the tricyclic groups (i.e. 1,4-Dihydro-indeno[1,2-c]pyrazole-Pyridin-2-yl Group, 4,5-Dihydro-1H-benzo[g]indazole-Pyridin-2-yl Group, 1,4,5,6-Tetrahydro-1,2-diaza-benzo[e]azulene-Pyridin-2-yl Group, 3H-8-Oxa-2,3-diaza-cyclopenta[a]indene-Pyridin-2-yl Group, 1,4-Dihydro-5-oxa-1,2-diaza-cyclopenta[a]naphthalene-Pyridin-2-yl Group, 1H-Benzo[4,5]thieno[3,2-c]pyrazole-Pyridin-2-yl Group, 1,4-Dihydro-5-thia-1,2-diaza-cyclopenta[a]naphthalene-Pyridin-2-yl Group, 1H-Benzo[4,5]thieno[3,2-c]pyrazole 4-oxide-Pyridin-2-yl Group, 1,4-Dihydro-5-thia-1,2-diaza-cyclopenta[a]naphthalene 5-oxide-Pyridin-2-yl Group, 1H-Benzo[4,5]thieno[3,2-c]pyrazole 4,4-dioxide-Pyridin-2-yl Group, 1,4-Dihydro-5-thia-1,2-diaza-cyclopenta[a]naphthalene 5,5-dioxide-Pyridin-2-yl Group, 1,4-Dihydro-pyrazolo[4,3-b]indole-Pyridin-2-yl Group and 4,5-Dihydro-1H-pyrazolo[4,3-c]quinoline-Pyridin-2-yl Group).

Subgeneric embodiments of the present invention of the Pyridin-3-yl-sulfonyl Group of compounds are expressly contemplated by the present invention. Such subgeneric embodiments within the Pyridin-3-yl-sulfonyl Group of compounds include the Pyridin-3-yl-sulfonyl Group in combination with each of the tricyclic groups (i.e. 1,4-Dihydro-indeno[1,2-c]pyrazole-Pyridin-3-yl Group, 4,5-Dihydro-1H-benzo[g]indazole-Pyridin-3-yl Group, 1,4,5,6-Tetrahydro-1,2-diaza-benzo[e]azulene-Pyridin-3-yl Group, 3H-8-Oxa-2,3-diaza-cyclopenta[a]indene-Pyridin-3-yl Group, 1,4-Dihydro-5-oxa-1,2-diaza-cyclopenta[a]naphthalene-Pyridin-3-yl Group, 1H-Benzo[4,5]thieno[3,2-c]pyrazole-Pyridin-3-yl Group, 1,4-Dihydro-5-thia-1,2-diaza-cyclopenta[a]naphthalene-Pyridin-3-yl Group, 1H-Benzo[4,5]thieno[3,2-c]pyrazole 4-oxide-Pyridin-3-yl Group, 1,4-Dihydro-5-thia-1,2-diaza-cyclopenta[a]naphthalene 5-oxide-Pyridin-3-yl Group, 1H-Benzo[4,5]thieno[3,2-c]pyrazole 4,4-dioxide-Pyridin-3-yl Group, 1,4-Dihydro-5-thia-1,2-diaza-cyclopenta[a]naphthalene 5,5-dioxide-Pyridin-3-yl Group, 1,4-Dihydro-pyrazolo[4,3-b]indole-Pyridin-3-yl Group and 4,5-Dihydro-1H-pyrazolo[4,3-c]quinoline-Pyridin-3-yl Group).

Subgeneric embodiments of the present invention of the Pyridazin-2-yl-sulfonyl Group of compounds are expressly contemplated by the present invention. Such subgeneric embodiments within the Pyridazin-2-yl-sulfonyl Group of compounds include the Pyridazin-2-yl-sulfonyl Group in combination with each of the tricyclic groups (i.e. 1,4-Dihydro-indeno[1,2-c]pyrazole-Pyridazin-2-yl Group, 4,5-Dihydro-1H-benzo[g]indazole-Pyridazin-2-yl Group, 1,4,5,6-Tetrahydro-1,2-diaza-benzo[e]azulene-Pyridazin-2-yl Group, 3H-8-Oxa-2,3-diaza-cyclopenta[a]indene-Pyridazin-2-yl Group, 1,4-Dihydro-5-oxa-1,2-diaza-cyclopenta[a]naphthalene-Pyridazin-2-yl Group, 1H-Benzo[4,5]thieno[3,2-c]pyrazole-Pyridazin-2-yl Group, 1,4-Dihydro-5-thia-1,2-diaza-cyclopenta[a]naphthalene-Pyridazin-2-yl Group, 1H-Benzo[4,5]thieno[3,2-c]pyrazole 4-oxide-Pyridazin-2-yl Group, 1,4-Dihydro-5-thia-1,2-diaza-cyclopenta[a]naphthalene 5-oxide-Pyridazin-2-yl Group, 1H-Benzo[4,5]thieno[3,2-c]pyrazole 4,4-dioxide-Pyridazin-2-yl Group, 1,4-Dihydro-5-thia-1,2-diaza-cyclopenta[a]naphthalene 5,5-dioxide-Pyridazin-2-yl Group, 1,4-Dihydro-pyrazolo[4,3-b]indole-Pyridazin-2-yl Group and 4,5-Dihydro-1H-pyrazolo[4,3-c]quinoline-Pyridazin-2-yl Group). One skilled in the art will appreciate that each of the preferences described below can be applied to each of the embodiments described above.

Preferred compounds of the invention are those compounds of formula I wherein $R^4$, $R^7$ and $R^8$ are independently selected from hydrogen, methyl, fluoro, chloro and bromo.

Other preferred compounds of the invention are those compounds of formula I wherein p is zero or one and $R^3$ is hydrogen, methyl, ethyl, trifluoromethyl, methoxy, trifluoromethoxy, amino carbonyl, fluoro, chloro or bromo, more preferably hydrogen, methyl or methoxy, most preferably hydrogen or methoxy.

Other preferred compounds of the invention are those compounds of formula I wherein $R^5$, $R^6$ and $R^9$ are independently selected from hydrogen, methyl, fluoro, chloro and bromo, more preferably hydrogen and methyl.

Other preferred compounds of this invention are those of the formula (I) wherein X is —N— and Y is >$CR^8$.

More preferred compounds of this invention are those of the formula (I) wherein X is >$CR^7$ and Y is —N—.

Other preferred compounds of this invention are those of the formula (I) wherein $R^2$ is methyl.

Other preferred compounds of this invention are those of the formula (I) wherein Z is >$CHR^9$ and n is zero.

Most preferred compounds of this invention are those of the formula (I) wherein Z is >$CHR^9$ and n is one.

Other compounds of this invention are those of the formula (I) wherein Z is —O—, more preferably wherein n is 1 or 2, most preferably wherein n is one.

Other compounds of this invention are those of the formula (I) wherein Z is —S—, >SO or >$SO_2$, more preferably wherein n is 1 or 2, most preferably wherein n is one.

Other compounds of this invention are those of the formula (I) wherein Z is >$NR^{10}$, more preferably wherein n is 1 or 2, most preferably wherein n is one.

Examples of specific preferred compounds of the formula I are the following 1-(5-Methanesulfonyl-pyridin-2-yl)-7-methoxy-3-trifluoromethyl-4,5-dihydro-1H-benzo[g]indazole, 1-(5-Methanesulfonyl-pyridin-2-yl)-3-trifluoromethyl-4,5-dihydro-1H-benzo[g]indazole, 1-(5-Methanesulfonyl-pyridin-2-yl )-6-methoxy-3-trifluoromethyl-1,4-dihydro-indeno[1,2-c]pyrazole, 3-Difluoromethyl-1-(5-methanesulfonyl-pyridin-2-yl)-7-methoxy-4,5-dihydro-1H-benzo[g]indazole and 1-(5-Methanesulfonyl-pyridin-2-y)-3-trifluoromethyl-4,5,5a,6,7,8,9,9a-octahydro-1H-benzo[g]indazole.

Other compounds of formula I include the following:

1-(5-Methanesulfonyl-pyridin-2-y)-8-methoxy-3-trifluoromethyl-4,5-dihydro-1H-benzo[g]indazole, 1-(5-Methanesulfonyl-pyridin-2-y)-5-methyl-3-trifluoromethyl-4,5-dihydro-1H-benzo[g]indazole, 1-(6-Methanesulfonyl-pyridin-3-yl)-3-trifluoromethyl-4,5-dihydro-1H-benzo[g]indazole, 2-(5-Methanesulfonyl-pyridin-2-yl)-3-trifluoromethyl-4,5,5a,6,7,8,9,9a-octahydro-2H-benzo[g]indazole, 1-(5-Methanesulfonyl-pyridin-2-yl)-3-trifluoromethyl-1,4,5,6-tetrahydro-1,2-diaza-benzo[e]azulene, 1-(5-Methanesulfonyl-pyridin-2-yl)-3-trifluoromethyl-1,4-dihydro-5-thia-1,2-diaza-cyclopenta[a]naphthalene, 3-Difluoromethyl-1-(5-methanesulfonyl-pyridin-2-yl)-1,4,5,6-tetrahydro-1,2-diaza-benzo[e]azulene, 1-(5-Methanesulfonyl-pyridin-2-yl)-3-trifluoromethyl-1,4-dihydro-5-oxa-1,2-diaza-cyclopenta[a]naphthalene, and 2-[3-Difluoromethyl-5-(7-methoxy-benzofuran-2-yl)-pyrazol-1-yl]-5-methanesulfonyl-pyridine.

The present invention also relates to a pharmaceutical composition for the treatment of a condition selected from the group consisting of arthritis (including osteoarthritis, degenerative joint disease, spondyloarthropathies, gouty arthritis, systemic lupus erythematosus, juvenile arthritis and rheumatoid arthritis), fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in cats), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock) and septic shock in a mammal, preferably a human, cat, livestock or a dog, comprising an amount of a compound of formula I or a pharmaceutically acceptable salt thereof effective in such treatment and a pharmaceutically acceptable carrier.

The present invention also relates to a pharmaceutical composition for the treatment of a disorder or condition that can be treated by selectively inhibiting COX-2 in a mammal, preferably a human, cat, livestock or dog (preferably a dog), comprising a COX-2 selective inhibiting effective amount of a compound of formula I or a pharmaceutically acceptable salt thereof and a pharmaceutically acceptable carrier.

The present invention also relates to a method for treating a condition selected from the group consisting of arthritis (including osteoarthritis, degenerative joint disease, spondyloarthropathies, gouty arthritis, systemic lupus erythematosus, juvenile arthritis and rheumatoid arthritis), fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in cats), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock) and septic shock in a mammal, preferably a human, cat, livestock or a dog (preferably a dog), comprising administering to said mammal an amount of a compound of formula I or a pharmaceutically acceptable salt thereof effective in treating such a condition.

The present invention also relates to a method for treating a disorder or condition that can be treated or prevented by selectively inhibiting COX-2 in a mammal, preferably a human, cat, livestock or a dog (more preferably a dog), comprising administering to a mammal requiring such treatment a COX-2 selective inhibiting effective amount of a compound of formula I or a pharmaceutically acceptable salt thereof.

This invention also relates to a method of or a pharmaceutical composition for treating inflammatory processes and diseases comprising administering a compound of formula I of this invention or its salt to a mammal including a human, cat, livestock or dog (preferably a dog), wherein said inflammatory processes and diseases are defined as above, and said inhibitory compound is used in combination with one or more other therapeutically active agents under the following conditions:

A.) where a joint has become seriously inflamed as well as infected at the same time by bacteria, fungi, protozoa, and/or virus, said inhibitory compound is administered in combination with one or more antibiotic, antifungal, antiprotozoal, and/or antiviral therapeutic agents;

B.) where a multi-fold treatment of pain and inflammation is desired, said inhibitory compound is administered in combination with inhibitors of other mediators of inflammation, comprising one or more members independently selected from the group consisting essentially of:
(1) NSAID's;
(2) $H_1$-receptor antagonists;
(3) kinin-$B_1$- and $B_2$-receptor antagonists;
(4) prostaglandin inhibitors selected from the group consisting of PGD-, PGF- $PGI_2$-, and PGE-receptor antagonists;
(5) thromboxane $A_2$ ($TXA_2$-) inhibitors;
(6) 5-, 12- and 15-lipoxygenase inhibitors;
(7) leukotriene $LTC_4$-, $LTD_4/LTE_4$-, and $LTB_4$- inhibitors;
(8) PAF-receptor antagonists;
(9) gold in the form of an aurothio group together with one or more hydrophilic groups;

(10) immunosuppressive agents selected from the group consisting of cyclosporine, azathioprine, and methotrexate;
(11) anti-inflammatory glucocorticoids;
(12) penicillamine;
(13) hydroxychloroquine;
(14) anti-gout agents including colchicine; xanthine oxidase inhibitors including allopurinol; and uricosuric agents selected from probenecid, sulfinpyrazone, and benzbromarone;

C.) where older mammals are being treated for disease conditions, syndromes and symptoms found in geriatric mammals, said inhibitory compound is administered in combination with one or more members independently selected from the group consisting essentially of:
  (1) cognitive therapeutics to counteract memory loss and impairment;
  (2) anti-hypertensives and other cardiovascular drugs intended to offset the consequences of atherosclerosis, hypertension, myocardial ischemia, angina, congestive heart failure, and myocardial infarction, selected from the group consisting of:
    a. diuretics;
    b. vasodilators;
    c. β-adrenergic receptor antagonists;
    d. angiotensin-II converting enzyme inhibitors (ACE-inhibitors), alone or optionally together with neutral endopeptidase inhibitors;
    e. angiotensin II receptor antagonists;
    f. renin inhibitors;
    g. calcium channel blockers;
    h. sympatholytic agents;
    i. $\alpha_2$-adrenergic agonists;
    j. α-adrenergic receptor antagonists; and
    k. HMG-CoA-reductase inhibitors (anti-hypercholesterolemics);
  (3) antineoplastic agents selected from:
    a. antimitotic drugs selected from:
      i. vinca alkaloids selected from:
        [1] vinblastine, and
        [2] vincristine;
  (4) growth hormone secretagogues;
  (5) strong analgesics;
  (6) local and systemic anesthetics; and
  (7) $H_2$-receptor antagonists, proton pump inhibitors, and other gastroprotective agents.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "livestock animals" as used herein refers to domesticated quadrupeds, which includes those being raised for meat and various byproducts, e.g., a bovine animal including cattle and other members of the genus Bos, a porcine animal including domestic swine and other members of the genus Sus, an ovine animal including sheep and other members of the genus Ovis, domestic goats and other members of the genus Capra; domesticated quadrupeds being raised for specialized tasks such as use as a beast of burden, e.g., an equine animal including domestic horses and other members of the family Equidae, genus Equus, or for searching and sentinel duty, e.g., a canine animal including domestic dogs and other members of the genus Canis; and domesticated quadrupeds being raised primarily for recreational purposes, e.g., members of Equus and Canis, as well as a feline animal including domestic cats and other members of the family Felidae, genus Felis.

"Companion animals" as used herein refers to horses, cats and dogs. As used herein, the term "dog(s)" denotes any member of the species Canis familiaris, of which there are a large number of different breeds. While laboratory determinations of biological activity may have been carried out using a particular breed, it is contemplated that the inhibitory compounds of the present invention will be found to be useful for treating pain and inflammation in any of these numerous breeds. Dogs represent a particularly preferred class of patients in that they are well known as being very susceptible to chronic inflammatory processes such as osteoarthritis and degenerative joint disease, which in dogs often results from a variety of developmental diseases, e.g., hip dysplasia and osteochondrosis, as well as from traumatic injuries to joints. Conventional NSAID's, if used in canine therapy, have the potential for serious adverse gastrointestinal reactions and other adverse reactions including kidney and liver toxicity. Gastrointestinal effects such as single or multiple ulcerations, including perforation and hemorrhage of the esophagus, stomach, duodenum or small and large intestine, are usually debilitating, but can often be severe or even fatal.

The term "treating reproductive disorders (preferably in livestock)" as used herein refers to the use of the COX-2 inhibitors of the invention in mammals, preferably livestock animals (cattle, pigs, sheep, goats or horses) during the estrus cycle to control the time of onset of estrus by blocking the uterine signal for lysis of the corpus luteum, i.e. F-series prostaglandins, then removing the inhibition when the onset of estrus is desired. There are settings where it is useful to control or synchronize the time of estrus, especially when artificial insemination or embryo transfer are to be performed. Such use also includes enhancing the rate of embryo survival in pregnant livestock animals. Blocking F-series prostaglandin release can have several beneficial actions including reducing uterine contractions, enhancing uteroplacental bloodflow, supporting recognition of pregnancy, and postponing lysis of the corpus luteum at the time when estrus would have occurred had the animal not become pregnant (around Day 21 of pregnancy). Such treatment also abrogates the effects of stress on reproduction. For example reductions in fertility caused by excessive heat, negative energy balance and other stresses which have a COX-2 mediated component, as does abortion induced by stress such as heat, transportation, co-mingling, palpation, infection, etc. Such treatment is also useful to control the time of parturition, which is accompanied by release of F-series prostaglandins that lead to lysis of the corpus luteum. Inhibition of COX-2 would block the onset of premature labor in livestock animals, allowing the offspring time to mature before birth. Also there are settings where controlling the time of parturition is a useful tool for management of pregnant animals.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic and diagnostic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing prodrugs of compounds of the formula I. This invention also encompasses methods of treating or preventing disorders that can be treated or prevented by the selective inhibition of COX-2 comprising administering prodrugs of compounds of the formula I. Compounds of formula I having free amino, amido, hydroxy, carboxylic acid ester, sulfonamide or carboxylic groups (especially alkyl-S— and alkyl-(S=O)—) can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters are covalently bonded to the above substituents of formula I through the carbonyl carbon prodrug sidechain. Prodrugs also include metabolically labile groups such as ethers, acetates, mercaptans and sulfoxides.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies and TNF receptor immunoglobulin molecules (such as Enbrel®), low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The active ingredient (i.e. the compounds of formula I) of the present invention may be administered in combination with inhibitors of other mediators of inflammation, comprising one or more members selected from the group consisting essentially of the classes of such inhibitors and examples thereof which include, matrix metalloproteinase inhibitors, aggrecanase inhibitors, TACE inhibitors, leucotriene receptor antagonists, IL-1 processing and release inhibitors, IL-1 ra, H$_1$-receptor antagonists; kinin-B$_1$- and B$_2$-receptor antagonists; prostaglandin inhibitors such as PGD-, PGF- PGI$_2$-, and PGE-receptor antagonists; thromboxane A$_2$ (TXA2-) inhibitors; 5- and 12-lipoxygenase inhibitors; leukotriene LTC$_4$-, LTD$_4$/LTE$_4$-, and LTB$_4$-inhibitors; PAF-receptor antagonists; gold in the form of an aurothio group together with various hydrophilic groups; immunosuppressive agents, e.g., cyclosporine, azathioprine, and methotrexate; anti-inflammatory glucocorticoids; penicillamine; hydroxychloroquine; anti-gout agents, e.g., colchicine, xanthine oxidase inhibitors, e.g., allopurinol, and uricosuric agents, e.g., probenecid, sulfinpyrazone, and benzbromarone.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with anti-hypertensives and other cardiovascular drugs intended to offset the consequences of atherosclerosis, including hypertension, myocardial ischemia including angina, congestive heart failure, and myocardial infarction, selected from vasodilators such as hydralazine, β-adrenergic receptor antagonists such as propranolol, calcium channel blockers such as nifedipine, α$_2$-adrenergic agonists such as clonidine, α-adrenergic receptor antagonists such as prazosin, and HMG-CoA-reductase inhibitors (anti-hypercholesterolemics) such as lovastatin or atorvastatin.

The active ingredient of the present invention may also be administered in combination with one or more antibiotic, antifungal, antiprotozoal, antiviral or similar therapeutic agents.

The compounds of the present invention may also be used in combination with CNS agents such as antidepressants (such as sertraline), anti-Parkinsonian drugs (such as L-dopa, requip, mirapex, MAOB inhibitors such as selegine and rasagiline, comP inhibitors such as Tasmar, A-2 inhibitors, dopamine reuptake inhibitors, NMDA antagonists, nicotine agonists, dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, lasofoxifene, droloxifene or fosomax and immunosuppressant agents such as FK-506 and rapamycin.

The present invention also relates to the formulation of the active agents of the present invention alone or with one or more other therapeutic agents which are to form the intended combination, including wherein said different drugs have varying half-lives, by creating controlled-release forms of said drugs with different release times which achieves relatively uniform dosing; or, in the case of non-human patients, a medicated feed dosage form in which said drugs used in the combination are present together in admixture in said feed composition. There is further provided in accordance with the present invention co-administration in which the combination of drugs is achieved by the simultaneous administration of said drugs to be given in combination; including co-administration by means of different dosage forms and routes of administration; the use of combinations in accordance with different but regular and continuous dosing schedules whereby desired plasma levels of said drugs involved are maintained in the patient being treated, even though the individual drugs making up said combination are not being administered to said patient simultaneously.

DETAILED DESCRIPTION OF THE INVENTION

Compounds of the formula I may be prepared according to the following reaction schemes and discussion. Unless otherwise indicated, $R^1$ through $R^8$, X and n in the reaction schemes and discussion that follow are as defined above.

SCHEME 1

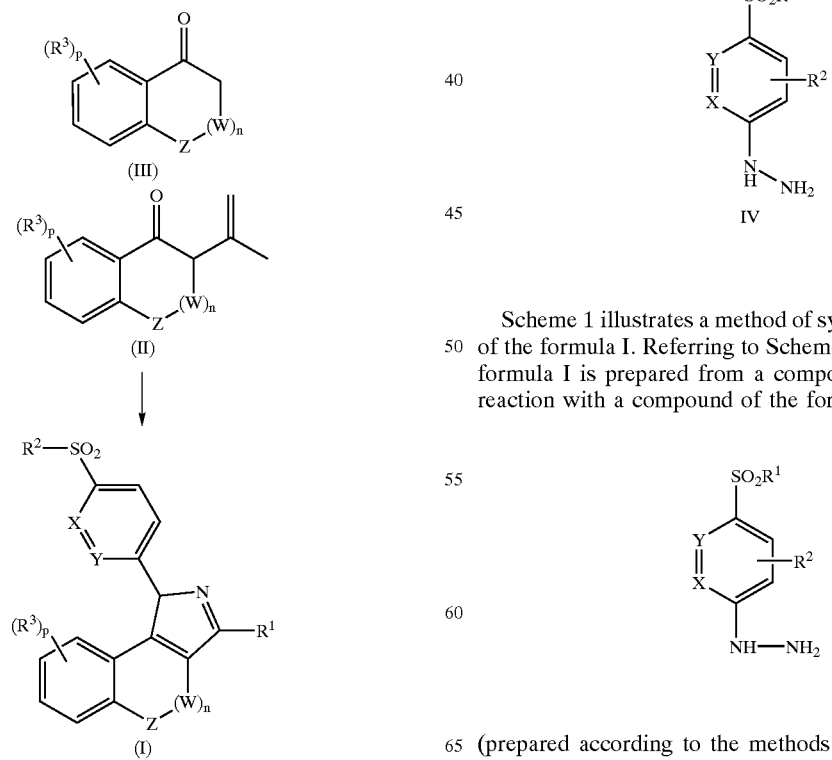

SCHEME 2

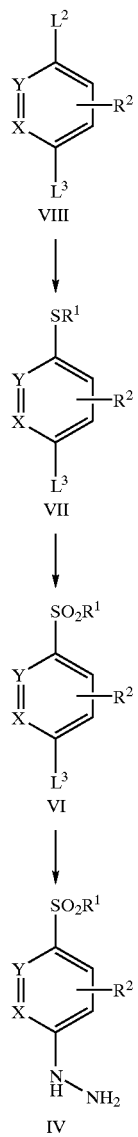

Scheme 1 illustrates a method of synthesizing compounds of the formula I. Referring to Scheme 1, a compound of the formula I is prepared from a compound of formula II, by reaction with a compound of the formula

IV

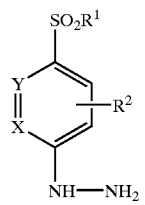

(prepared according to the methods of Scheme 2 or commercially available or prepared by methods known to those skilled in the art such as F. Walker et al., *J. Chem. Soc.* 1939

(1948)) under acidic, neutral, or basic conditions preferably in the presence of acid or the acid salt of the compound of formula IV in a suitable solvent. Suitable solvents include alcohols, such as ethanol, methanol, propanol, isopropanol, trifluoroethanol or butanol; dimethyl sulfoxide (DMSO), N,N-dimethylformamide (DMF), N,N-dimethylacetamide (DMA) or N-methyl-2-pyrrolidinone (NMP), preferably an alcohol, most preferably ethanol trifluoroethanol, or isopropanol. Suitable acids include hydrochloric acid, trifluoroacetic acid, acetic acid, and sulfuric acid. This reaction is generally carried out at a temperature from about 0° C. to about 140° C., preferably at about the reflux temperature of the polar solvent.

The compound of formula II is prepared from a compound of the formula III by reaction with a compound of the formula

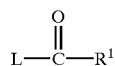

V wherein L is a leaving group, in the presence of a base and a solvent. Examples of compounds of formula V include ester or ester equivalents such as acylimidazole, dialkylamide and dialkylacetal, preferably ester and acylimidazole. Suitable bases include potassium carbonate ($K_2CO_3$), sodium carbonate ($Na_2CO_3$), sodium hydride (NaH), sodium methoxide, potassium-tert-butoxide, lithium diisopropylamide, pyrrolidine and piperidine, preferably sodium methoxide. These reactions can be carried out in a solvent such as di-(alkyl)ether (preferably dimethylether), tetrahydrofuran (THF), methanol, dichloromethane, methyl tert-butyl ether, dimethylformamide (DMF), dimethylacetamide (DMA) or DMSO, preferably dimethoxyethane (DME). Reaction temperatures can range from about 0° C. to about 150° C., preferably from about 20° C. to about 25° C.

Compounds of formula III, IV and V are commercially available or can be made by methods well known to those of ordinary skill in the art. Compounds of formula III can be prepared by methods described in the literature, such as *Bulletin of the Chemical Society*, 63, 272 (1990); *J. Heterocyclic Chem.*, 25, 523 (1988) and *J. Org. Chem.*, 51 (22) 4250 (1986), each of which are incorporated by reference in their entirety.

Scheme 2 refers to the preparation of compounds of the formula IV which are intermediates used in Scheme 1. Referring to Scheme 2, compounds of the formula IV are prepared from compounds of the formula VI by reaction with hydrazine in the presence of a polar solvent. Suitable solvents include alcohols, such as ethanol, methanol, propanol or butanol; dimethyl sulfoxide (DMSO), N,N-dimethylformamide (DMF), N,N-dimethylacetamide (DMA) or N-methyl-2-pyrrolidinone (NMP), preferably an alcohol, most preferably ethanol. This reaction is generally carried out at a temperature from about 0° C. to about 140° C., preferably at about the reflux temperature of the polar solvent. Preferably the product is isolated as a salt, such as a hydrochoride salt.

The compound of formula VI is prepared from a compound of the formula VII by reaction with an oxidizing reagent in the presence of a solvent. Suitable oxidants include meta-chloroperbenzoic acid, hydrogen peroxide, sodium perborate, or Oxone® (Oxone® is preferred). Suitable solvents or solvent mixtures include methanol-water, dioxane-water, tetrahydrofuran-water, methylene chloride, or chloroform, preferably methanol-water. Suitable temperatures for the aforesaid reaction range from about 0° C. to about 60° C., preferably the temperature may range from about 20° C. to about 25° C. (i.e. room temperature). The reaction is complete within about 0.5 hours to about 24 hours, preferably about 16 hours.

The compound of the formula VII is prepared from a compound of formula VIII by reaction with a disulfide or methyl alkylthiolsulfonate of the formula $R^1S$-L, wherein L is alkylthio or methylsulfonate, in the presence or absence of a base in a polar solvent. Suitable bases include, alkyllithium such as n-butyllithium, and suitable solvents include ether, benzene and THF. This reaction is generally carried out at a temperature from about −78° C. to 0° C. for from about 1 to 8 hours.

Compounds of the formula VIII are commercially available or can be made by methods well known to those of ordinary skill in the art.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., wherein $R^2$ $R^4$, $R^5$ or $R^6$ include a —COOH, tetrazole or other acidic moiety, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Method for Assessing Biological Activities

The activity of the compounds of the formula (I) of the present invention can be demonstrated by the following assays.

Human In vitro Assays

Human Cell-Based COX-1 Assay

Human peripheral blood obtained from healthy volunteers was diluted to 1/10 volume with 3.8% sodium citrate solution. The platelet-rich plasma immediately obtained is washed with 0.14 M sodium chloride containing 12 mM Tris-HCl (pH 7.4) and 1.2 mM EDTA. Platelets are then washed with platelet buffer (Hanks buffer (Ca free) containing 0.2% BSA and 20 mM Hepes). Finally, the human washed platelets (HWP) are suspended in platelet buffer at the concentration of $2.85 \times 10^8$ cells/ml and stored at room temperature until use. The HWP suspension (70 μl aliquots, final $2.0 \times 10^7$ cells/ml) is placed in a 96-well U bottom plate and 10 μl aliquots of 12.6 mM calcium chloride added. Platelets are incubated with A23187 (final 10 μM, Sigma) with test compound (0.1–100 μM) dissolved in DMSO (final concentration; less than 0.01%) at 37° C. for 15 minutes. The reaction is stopped by addition of EDTA (final 7.7 mM) and TxB2 in the supernatant quantitated by using a radioimmunoassay kit (Amersham) according to the manufacturer's procedure.

Human Cell-Based COX-2 Assay

The human cell based COX-2 assay can be carried out as previously described (Moore et al., *Inflam. Res.*, 45, 54, 1996). Confluent human umbilical vein endothelial cells (HUVECs, Morinaga) in a 96-well flat bottom plate are washed with 80 ml of RPMI1640 containing 2% FBS and incubated with hIL-1β (final concentration 300 U/ml, R & D Systems) at 37° C. for 24 hours. After washing, the activated HUVECs are incubated with test compound (final concentration; 0.1 nM-1 μM) dissolved in DMSO (final concentration; less than 0.01%) at 37° C. for 20 minutes and stimulated with A23187 (final concentration 30 mM) in Hanks buffer containing 0.2% BSA, 20 mM Hepes at 37° C. for 15 minutes. 6-Keto-PGF$_{1\alpha}$, stable metabolite of PGI2, in the supernatant is quantitated by using a radioimmunoassay method (antibody; Preseptive Diagnostics, SPA; Amersham).

Canine in vitro Assays

The following canine cell based COX 1 and COX-2 assays have been reported in Ricketts et al., *Evaluation of Selective Inhibition of Canine Cyclooxygenase 1 and 2 by Carprofen and Other Nonsteroidal Anti-inflammatory Drugs*, American Journal of Veterinary Research, 59 (11), 1441–1446.

Protocol for Evaluation of Canine COX-1 Activity

Test drug compounds are solubilized and diluted the day before the assay was to be conducted with 0.1 mL of DMSO/9.9 mL of Hank's balanced salts solution (HBSS), and stored overnight at 4° C. On the day that the assay is carried out, citrated blood is drawn from a donor dog, centrifuged at 190×g for 25 minutes at room temperature, and the resulting platelet-rich plasma is then transferred to a new tube for further procedures. The platelets are washed by centrifuging at 1500×g for 10 minutes at room temperature. The platelets are washed with platelet buffer comprising Hank's buffer (Ca free) with 0.2% bovine serum albumin (BSA) and 20 mM HEPES. The platelet samples are then adjusted to $1.5 \times 10^7$/mL, after which 50 μl of calcium ionophore (A23187) together with a calcium chloride solution are added to 50 μl of test drug compound dilution in plates to produce final concentrations of 1.7 μM A23187 and 1.26 mM Ca. Then, 100 μl of canine washed platelets are added and the samples were incubated at 37° C. for 15 minutes, after which the reaction is stopped by adding 20 μl of 77 mM EDTA. The plates are then centrifuged at 2000×g for 10 minutes at 4° C., after which 50 μl of supernatant is assayed for thromboxane $B_2$ ($TXB_2$) by enzyme-immunoassay (EIA). The pg/mL of $TXB_2$ can be calculated from the standard line included on each plate, from which it is possible to calculate the percent inhibition of COX-1 and the $IC_{50}$ values for the test drug compounds.

Protocol for Evaluation of Canine COX-2 Activity

A canine histocytoma (macrophage-like) cell line from the American Type Culture Collection designated as DH82, is used in setting up the protocol for evaluating the COX-2 inhibition activity of various test drug compounds. There is added to flasks of these cells 10 μg/mL of LPS, after which the flask cultures are incubated overnight. The same test drug compound dilutions as described above for the COX-1 protocol are used for the COX-2 assay and are prepared the day before the assay is carried out. The cells are harvested from the culture flasks by scraping, and are then washed with minimal Eagle's media (MEM) combined with 1% fetal bovine serum, centrifuged at 1500 rpm for 2 minutes, and adjusted to a concentration of $3.2 \times 10^5$ cells/mL. To 50 μl of test drug dilution there is added 50 μl of arachidonic acid in MEM to give a 10 μM final concentration, and there is added as well 100 μl of cell suspension to give a final concentration of $1.6 \times 10^5$ cells/mL. The test sample suspensions were incubated for 1 hour and then centrifuged at 1000 rpm for 10 minutes at 4° C., after which 50 μl aliquots of each test drug sample are delivered to EIA plates. The EIA was performed for prostaglandin $E_2$ ($PGE_2$), and the pg/mL concentration of $PGE_2$ is calculated from the standard line included on each plate. From this data it is possible to calculate the percent inhibition of COX-2 and the $IC_{50}$ values for the test drug compounds. Repeated investigations of COX-1 and COX-2 inhibition were conducted over the course of several months. The results are averaged, and a single COX-1:COX-2 ratio is calculated.

Whole blood assays for COX-1 and COX-2 are known in the art such as the methods described in C. Brideau, et al., *A Human Whole Blood Assay for Clinical Evaluation of Biochemical Efficacy of Cyclooxygenase Inhibitors, Inflammation Research*, Vol. 45, pp. 68–74 (1996). These methods may be applied with feline, canine or human blood as needed.

In vivo Assays

Carrageenan Induced Foot Edema in Rats

Male Sprague-Dawley rats (5 weeks old, Charles River Japan) are fasted overnight. A line is drawn using a marker above the ankle on the right hind paw and the paw volume (V0) is measured by water displacement using a plethysmometer (Muromachi). Animals are given orally either vehicle (0.1% methyl cellulose or 5% Tween 80) or a test compound (2.5 ml per 10 μg body weight). One hour later, the animals are then injected intradermally with λ-carrageenan (0.1 ml of 1% w/v suspension in saline, Zushikagaku) into right hind paw (Winter et al., *Proc. Soc.*

*Exp. Biol. Med.,* 111, 544, 1962; Lombardino et al.,*Arzneim. Forsch.,* 25, 1629, 1975) and three hours later, the paw volume (V3) is measured and the increase in volume (V3–V0) calculated. Since maximum inhibition attainable with classical NSAID's is 60–70%, $ED_{30}$ values can be calculated.

Gastric Ulceration in Rats

The gastric ulcerogenicity of test compound can be assessed by a modification of the conventional method (Ezer et al., *J. Pharm. Pharmacol.,* 28, 655, 1976; Cashin et al., *J. Pharm. Pharmacol.,* 29, 330–336, 1977). Male Sprague-Dawley rats (5 weeks old, Charles River Japan), fasted overnight, are given orally either vehicle (0.1% methyl cellulose or 5% Tween 80) or a test compound (1 ml per 100 g body weight). Six hours after, the animals are sacrificed by cervical dislocation. The stomachs are removed and inflated with 1% formalin solution (10 ml). Stomachs are then opened by cutting along the greater curvature. From the number of rats that showed at least one gastric ulcer or hemorrhaging erosion (including ecchymosis), the incidence of ulceration can be calculated. Animals do not have access to either food or water during the experiment.

Canine Whole Blood ex vivo Determinations of COX-1 and COX-2 Activity Inhibition The in vivo inhibitory potency of a test compound against COX-1 and COX-2 activity may be evaluated using an ex vivo procedure on canine whole blood. Three dogs are dosed with 5 mg/kg of the test compound administered by oral gavage in 0.5% methylcellulose vehicle and three dogs are untreated. A zero-hour blood sample is collected from all dogs in the study prior to dosing, followed by 2- and 8-hour post-dose blood sample collections. Test tubes are prepared containing 2 $\mu$L of either (A) calcium ionophore A23187 giving a 50 $\mu$M final concentration, which stimulates the production of thromboxane $B_2$ ($TXB_2$) for COX-1 activity determination; or of (B) lipopolysaccharide (LPS) to give a 10 $\mu$g/mL final concentration, which stimulates the production of prostaglandin $E_2$ ($PGE_2$) for COX-2 activity determination. Test tubes with unstimulated vehicle are used as controls. A 500 $\mu$L sample of blood is added to each of the above-described test tubes, after which they are incubated at 37° C. for one hour in the case of the calcium ionophore-containing test tubes, and overnight in the case of the LPS-containing test tubes. After incubation, 10 $\mu$L of EDTA is added to give a final concentration of 0.3%, in order to prevent coagulation of the plasma which sometimes occurs after thawing frozen plasma samples. The incubated samples are centrifuged at 4° C. and the resulting plasma sample of ~200 $\mu$L is collected and stored at −20° C. in polypropylene 96-well plates. In order to determine endpoints for this study, enzyme immunoassay (EIA) kits available from Cayman can be used to measure production of $TXB_2$ and $PGE_2$, utilizing the principle of competitive binding of tracer to antibody and endpoint determination by colorimetry. Plasma samples are diluted to approximate the range of standard amounts which would be supplied in a diagnostic or research tools kit, i.e., 1/500 for $TXB_2$ and 1/750 for $PGE_2$.

Data Analysis

Statistical program packages, SYSTAT (SYSTAT, INC.) and StatView (Abacus Cencepts, Inc.) for Macintosh can be used. Differences between test compound treated group and control group are tested by using ANOVA. The IC50 (ED30) values were calculated from the equation for the log-linear regression line of concentration (dose) versus percent inhibition.

Most compounds prepared in the Working Examples as described hereinafter were tested by at least one of the methods described above, and showed $IC_{50}$ values of 0.001 $\mu$M to 3 $\mu$M with respect to inhibition of COX-2 in either the canine or human assays.

COX-2 selectivity can be determined by ratio in terms of $IC_{50}$ value of COX-1 inhibition to COX-2 inhibition. In general, it can be said that a compound showing a COX-2/COX-1 inhibition ratio of more than 5 has good COX-2 selectivity.

The compounds of the formula (I) of this invention can be administered via oral, parenteral, anal, buccal or topical routes to mammals (including humans, dogs, cats, horses and livestock).

In general, these compounds are most desirably administered to humans in doses ranging from 0.01 mg to 100 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of above-mentioned diseases.

These compounds are most desirably administered to said non-human mammals, e.g. dogs, cats, horses or livestock in an amount, expressed as mg per kg of body weight of said member per day, ranging from about 0.01 mg/kg to about 20.0 mg/kg/day, preferably from about 0.1 mg/kg to about 12.0 mg/kg/day, more preferably from about 0.5 mg/kg to about 10.0 mg/kg/day, and most preferably from about 0.5 mg/kg to about 8.0 mg/kg/day.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various combinations thereof.

A preferred composition for dogs comprises an ingestible liquid peroral dosage form selected from the group consisting of a solution, suspension, emulsion, inverse emulsion, elixir, extract, tincture, and concentrate, optionally to be added to the drinking water of the dog being treated. Any of these liquid dosage forms, when formulated in accordance with methods well known in the art, can either be administered directly to the dog being treated, or may be added to the drinking water of the dog being treated. The concentrate liquid form, on the other hand, is formulated to be added first to a given amount of water, from which an aliquot amount may be withdrawn for administration directly to the dog or addition to the drinking water of the dog.

A preferred composition provides delayed-, sustained-, and/or controlled-release of said anti-inflammatory selective COX-2 inhibitor. Such preferred compositions include all such dosage forms which produce $\geq 80\%$ inhibition of COX-2 isozyme activity and result in a plasma concentration of said inhibitor of at least 3 fold the COX-2 $IC_{50}$ for at least 4 hours; preferably for at least 8 hours; more preferably for at least 12 hours; more preferably still for at least 16 hours; even more preferably still for at least 20 hours; and most preferably for at least 24 hours. Preferably, there is included within the above-described dosage forms those which produce $\geq 80\%$ inhibition of COX-2 isozyme activity and result in a plasma concentration of said inhibitor of at least 5 fold the COX-2 $IC_{50}$ for at least 4 hours, preferably for at least 8 hours, more preferably for at least 12 hours, still more preferably for at least 20 hours, and most preferably for at least 24 hours. More preferably, there is included the above-described dosage forms which produce $\geq 90\%$ inhibition of COX-2 isozyme activity and result in a plasma concentration of said inhibitor of at least 5 fold the COX-2 $IC_{50}$ for at least 4 hours, preferably for at least 8 hours, more preferably for at least 12 hours, still more preferably for at least 20 hours, and most preferably for at least 24 hours.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of formula (I) may also be administered in the form of suppositories for rectal or vaginal administration of the active ingredient. These compositions can be prepared by mixing the active ingredient with a suitable non-irritating excipient which is solid at room temperature (for example, 10° C. to 32° C.) but liquid at the rectal temperature and will melt in the rectum or vagina to release the active ingredient. Such materials are polyethylene glycols, cocoa butter, suppository and wax.

For buccal administration, the composition may take the form of tablets or lozenges formulated in conventional manner.

For transdermal administration, transdermal patches prepared in accordance with well known drug delivery technology may be prepared and applied to the skin of a mammal, preferably a human or a dog, to be treated, whereafter the active agent by reason of its formulated solubility characteristics migrates across the epidermis and into the dermal layers of the skin where it is taken up as part of the general circulation, ultimately providing systemic distribution of the active ingredient over a desired, extended period of time. Also included are implants which are placed beneath the epidermal layer of the skin, i.e. between the epidermis and the dermis of the skin of the patient being treated. Such an implant will be formulated in accordance with well known principles and materials commonly used in this delivery technology, and may be prepared in such a way as to provide controlled-, sustained-, and/or delayed-release of the active ingredient into the systemic circulation of the patient. Such subepidermal (subcuticular) implants provide the same facility of installation and delivery efficiency as transdermal patches, but without the limitation of being subject to degradation, damage or accidental removal as a consequence of being exposed on the top layer of the patient's skin.

EXAMPLES

The following examples contain detailed descriptions of the methods of the preparation of compounds of formula (I). These detailed descriptions fall within the scope of the invention and serve to exemplify the above described general synthetic procedures which form part of the invention. These detailed descriptions are presented for illustrative purposes only and are not intended to restrict the scope of the present invention.

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath of up to 60° C.; reactions were monitored by thin layer chromatography (tlc) and reaction times are given for illustration only; melting points (m.p.) given are uncorrected (polymorphism may result in different melting points); structure and purity of all isolated compounds were assured by at least one of the following techniques: tlc (Merck silica gel 60 F-254 precoated plates), mass spectrometry, nuclear magnetic resonance (NMR) or infrared spectroscopy (IR). IR data were obtained on a FTIR 8200 (SHIMAZU Spectrometer). Yields are given for illustrative purposes only. Flash column chromatography was carried out using Merck silica gel 60 (230–400 mesh ASTM). Low-resolution mass spectral data (EI) were obtained on a Automass 120 (JEOL) mass spectrometer. Liquid Chromatography data was collected on a Hewlett Packard 1100 Liquid Chromatography/Mass Selective Detector (LC/MSD). Analysis was performed on a Luna C-18 column with dimensions of 3.0×150 mm. The flow rate was 0.425 ml/minute running a gradient of 50% 0.1% aqueous formic acid and 50% acetonitrile to 100% acetonitrile in 15 minutes. The ionization type for the mass detector of the Mass Spectrophotometer was atmospheric pressure electrospray in the positive ion mode with a fragmentor voltage of 50 volts. NMR data was determined at 270 MHz (JEOL JNM-LA 270 spectrometer) using deuterated chloroform (99.8% D), methanol (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc.

The following abbreviations are used:

| | |
|---|---|
| THF: | tetrahydrofuran |
| $CH_2Cl_2$: | dichloromethane |
| $NaHCO_3$: | sodium bicarbonate |
| HCl: | hydrogen chloride |
| $MgSO_4$: | magnesium sulfate |
| $Na_2SO_4$: | sodium sulfate |
| DME: | dimethoxyethane |
| n-BuLi: | n-butyllithium |
| DMF: | dimethylformamide |

Example 1

1-(5-methanesulfonyl-pyridin-2-yl)-3-trifluoromethyl-4,5-dihydro-1H-benzo[g]indazole Step 1: A solution mixture of the alpha tetralone (0.46 ml, 3.42 mmol) and ethyltrifluoroacetate (0.94 ml, 7.87 mmol) in dry dimethoxyethane (45 ml) at room temperature was treated with sodium methoxide (1.8 ml of 4.37 M, 7.87 mmol) and the reaction mixture vigorously stirred at room temperature for 21 hours. The reaction mixture was poured into aqueous 1N hydrochloric acid (20 ml) and extracted with ethyl acetate (50 ml×3), dried over magnesium sulfate (MgSO4), filtered, and concentrated in vacuo to give 723 mg (87%) the desired diketone as a dark brown oil.

Step 2: 5-Hydrazino-2-(methylsulfonyl)pyridine hydrochloride (75 mg, 0.34 mmol) and a drop of concentrated sulfuric acid was added to a solution of diketone from step 1 (89 mg, 0.37 mmol) in trifluoroethanol (3.5 mL). The mixture was heated at reflux temperature (85° C.) for 20 hours and cooled down to room temperature. The reaction mixture was poured into a saturated bicarbonate solution (20 ml) and extracted with ethyl acetate (20 ml×3). The organic layer was dried and concentrated in vacuo to give crude product as brown oil. The crude mixture was subjected to preparative thin layer chromatographic (TLC) (1000 um plate) purification eluting with 5% ethyl acetate:dichloromethane. The desired product was isolated after the band containing the product was washed with ethyl acetate and concentrated in vacuo to provide 70 mg (53%) of the product as a white solid.

Example 2

1-(6methanesulfonyl-pyridin-3-yl)-3-trifluoromethyl-4,5-dihydro-1H-bendzo[g]indazole The title compound was prepared according to the same procedure described above as step 2, Example 1, using 2-hydrazino-5-(methylsulfonyl)pyridine (63 mg) and diketone (Example 1, step 1, 89 mg) to provide the desired product (65 mg, 46%) as a white solid.

The compounds of Table 1 were prepared according to the same procedure described above in Example 1 substituting starting materials where appropriate.

TABLE 1

| EXAMPLE | MOLSTRUCTURE | HPLC RT | MASS (M + H) |
|---|---|---|---|
| 3 | 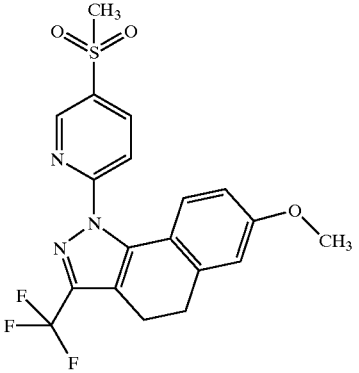 | 10.21 | 424 |
| 4 | 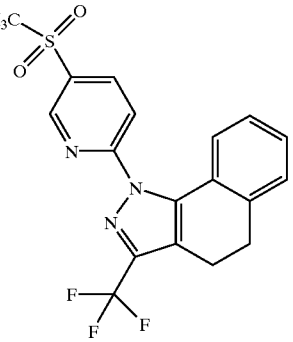 | 10.196 | 394 |

TABLE 1-continued

| EXAMPLE | MOLSTRUCTURE | HPLC RT | MASS (M + H) |
|---------|--------------|---------|--------------|
| 5 | | 10.36 | 424 |
| 6 | | 11.226 | 408 |
| 7 | | 11.352 | 410 |
| 8 | | 9.709 | 394 |

TABLE 1-continued

| EXAMPLE | MOLSTRUCTURE | HPLC RT | MASS (M + H) |
|---|---|---|---|
| 9 | | 8.341 | 405.43 |
| 10 | | 14.017 | 400 |
| 11 | | 11.5 | 407.42 |
| 12 | | 9.904 | 411.43 |

TABLE 1-continued

| EXAMPLE | MOLSTRUCTURE | HPLC RT | MASS (M + H) |
|---------|--------------|---------|--------------|
| 13 | | 9.54 | 389.43 |
| 14 | | 9.53 | 395.36 |
| 15 | | 8.179 | 393.44 |

Example 17

2-[3-difluoromethyl-5-(7-methoxy-benzofuran-2-yl)-pyrazol-1-yl]-5-methanesulfonyl-pyridine Step 1: A solution mixture of the thiochroman-4-one (500 mg, 3.04 mmol) and ethyldifluoroacetate (906 mg, 7.61 mmol) in dry dimethoxyethane (10 ml) at room temperature was treated with sodium methoxide (1.74 ml of 4.37 M, 7.61 mmol) and the reaction mixture vigorously stirred at room temperature for 6 hours. The reaction mixture was poured into aqueous 0.5N HCl (70 ml) and extracted with ethyl acetate (90 ml×2), dried (MgSO4), filtered, and concentrated in vacuo to give 810 mg (100%) of the desired diketone as a yellowish brown oil.

Step 2: 5-Hydrazino-2-(methylsulfonyl)pyridine hydrochloride (65 mg, 0.35 mmol) and a drop of concentrated sulfuric acid was added to a solution of diketone from step 1 (92.5 mg, 0.38 mmol) in trifluoroethanol (3.5 mL). The mixture was heated at reflux temperature (85° C.) for 24 hours and cooled down to room temperature. The reaction mixture was poured into a saturated bicarbonate solution (60 ml) and extracted with ethyl acetate (60 ml×2). The organic layer was dried and concentrated in vacuo to give crude product as brown oil. The crude mixture was subjected to preparative thin layer chromatographic (TLC) (1000 um plate) purification eluting with 5% ethyl acetate:dichloromethane. The desired product was isolated after the band containing the product was washed with ethyl acetate and concentrated in vacuo to provide 56.4 mg (41%) of the product as a white solid.

What is claimed is:

1. A compound of the formula

[Structure (I)]

wherein the dashed lines represent optional double bonds;
n is one;
p is an integer from one to two;
X is >$CR^7$ or —N—;
Y is >$CR^8$ or —N—;
Z is >$CHR^9$;
W is >$CR^5R^6$;
$R^1$ is —$CF_3$ or —$CHF_2$;
$R^2$ is ($C_1$–$C_6$)alkyl:
$R^3$ is hydrogen, halo, ($C_1$–$C_6$)alkyl, ($C_1$–$C_6$)alkenyl, ($C_1$–$C_6$)alkynyl, ($C_1$–$C_6$)alkoxy, —$OCF_3$, ($C_1$–$C_6$)alkylcarbonyl, formyl, formamidyl, cyano, ($C_1$–$C_6$)alkoxycarbonyl, aminocarbonyl, N-($C_1$–$C_6$)alkylaminocarbonyl or N,N-[($C_1$–$C_6$)alkyl]$_2$aminocarbonyl;
wherein said $R^3$ ($C_1$–$C_6$)alkyl may optionally be substituted with one to three substituents independently selected from halo, ($C_1$–$C_6$)alkoxy, cyano, ($C_1$–$C_6$)alkoxycarbonyl, aminocarbonycl, N-($C_1$–$C_6$)alkylaminocarbonyl and N,N-[($C_1$–$C_6$)alkyl]$_2$aminocarbonyl;
$R^4$ is hydrogen; halo; hydroxy; ($C_1$–$C_6$)alkyl; or ($C_1$–$C_6$)alkoxy optionally substituted with one to three halogen atoms;
wherein said $R^4$ ($C_1$–$C_6$)alkyl group may optionally be substituted with one to three substituents independently selected from halo, hydroxy, ($C_1$–$C_6$)alkoxy and cyano;
$R^5$ is hydrogen, halo, ($C_1$–$C_6$)alkyl, ($C_1$–$C_6$)alkoxy, ($C_1$–$C_6$)alkylcarbonyl, ($C_1$–$C_6$)alkoxycarbonyl or aminocarbonyl;
wherein said $R^5$ ($C_1$–$C_6$)alkyl group may optionally be substituted with one to three substituents independently selected from halo, hydroxy, ($C_1$–$C_6$)alkoxy and cyano;
$R^6$ is hydrogen, halo, ($C_1$–$C_6$)alkyl, ($C_1$–$C_6$)alkoxy, ($C_1$–$C_6$)alkylcarbonyl, ($C_1$–$C_6$)alkoxycarbonyl or aminocarbonyl;
$R^7$ is hydrogen; halo; hydroxy, ($C_1$–$C_6$)alkyl or ($C_1$–$C_6$)alkoxy optionally substituted with one to three halogen atoms;
wherein said $R^7$ ($C_1$–$C_6$)alkyl group may optionally be substituted with one three substituents independently selected from halo, hydroxy, ($C_1$–$C_6$)alkoxy and cyano;
$R^8$ is hydrogen; halo; hydroxy; ($C_1$–$C_6$)alkyl or ($C_1$–$C_6$)alkoxy optionally substituted with one to three halogen atoms;
wherein said $R^8$ ($C_1$–$C_6$)alkyl group may optionally be substituted with one to three substituents independently selected from halo, hydroxy, ($C_1$–$C_6$)alkoxy and cyano;
$R^9$ is hydrogen; halo; hydroxy; ($C_1$–$C_6$)alkyl or ($C_1$–$C_8$)alkoxy optionally substituted with one to three halogen atoms;
wherein said $R^9$ ($C_1$–$C_6$)alkyl group may optionally be substituted with one to three substituents independently selected from halo, hydroxy, ($C_1$–$C_6$)alkoxy or cyano;
$R^{10}$ is hydrogen, ($C_1$–$C_6$)alkyl, ($C_1$–$C_6$)alkylcarbonyl or aminocarbonyl;
wherein said $R^{10}$ ($C_1$–$C_6$)alkyl group may optionally be substituted with one to three substituents independently selected from halo, hydroxy, ($C_1$–$C_6$)alkoxy and cyano;
with the proviso that either 1) X is $CR^7$ and Y is —N— or 2) X is —N— and Y is $CR^8$, or a pharmaceutically acceptable salt of such a compound.

2. A compound according to claim 1 wherein X is $CR^7$ and Y is —N—.

3. A compound according to claim 1 wherein X is —N— and Y is $CR^8$.

4. A compound according to claim 1 wherein $R^2$ is methyl.

5. A compound according to claim 1 wherein said compound is selected from the group consisting of:

1-(5-Methanesulfonyl-pyridin-2-yl)-7-methoxy-3-trifluoromethyl-4,5-dihydro-1H-benzo[g]indazole, 1-(5-Methanesulfonyl-pyridin-2-yl)-3-trifluoromethyl-4,5-dihydro-1H-benzo[g]indazole, 3-Difluoromethyl-1-(5-methanesulfonyl-pyridin-2-yl)-7-methoxy-4,5-dihydro-1H-benzo[g]indazole and 1-(5-Methanesulfonyl-pyridin-2-yl)-3-trifluoromethyl-4,5,5a,6,7,8,9,9a-octahydro-1H-benzo[g]indazole.

6. A pharmaceutical composition for the treatment of arthritis and inflammation comprising an amount of a compound of claim 1 or a pharmaceutically acceptable salt thereof effective in such treatments and a pharmaceutically acceptable carrier.

7. A pharmaceutical composition for treating arthritis and inflammation by selectively inhibiting COX-2 in a mammal, comprising a COX-2 selective inhibiting effective amount of a compound according to claim 1, or a pharmaceutically acceptable salt thereof and a pharmaceutically acceptable carrier.

8. A method for treating arthritis and inflammation comprising administering to a mammal an amount of a compound according to claim 1 or a pharmaceutically acceptable salt thereof effective in treating arthritis.

9. A method for treating arthritis and inflammation by selectively inhibiting COX-2 in a mammal, comprising administering to a mammal requiring such treatment a COX-2 selective inhibiting effective amount of a compound according to claim 1, or a pharmaceutically acceptable salt thereof.

* * * * *